United States Patent [19]

Sorg

[11] 4,064,244
[45] Dec. 20, 1977

[54] ORGANIC COMPOUNDS

[75] Inventor: Dieter Sorg, Bern, Switzerland

[73] Assignee: Sandoz Ltd., Basel, Switzerland

[21] Appl. No.: 588,002

[22] Filed: June 18, 1975

Related U.S. Application Data

[63] Continuation of Ser. No. 437,348, Jan. 28, 1974, abandoned.

[30] Foreign Application Priority Data

Feb. 2, 1973  Switzerland .................... 1563/73

[51] Int. Cl.$^2$ .................. C07D 417/04; A61K 31/495
[52] U.S. Cl. ............................ 424/250; 260/268 H; 260/268 C
[58] Field of Search .................. 260/268 C, 268 H; 424/250

[56] References Cited

U.S. PATENT DOCUMENTS

| 2,543,972 | 7/1951 | Hultquist et al. | 260/268 H |
| 2,562,036 | 7/1951 | Hultquist et al. | 260/268 H |
| 2,606,906 | 8/1952 | Hultquist et al. | 260/268 H |
| 3,489,757 | 1/1970 | Koppe et al. | 260/268 H |

FOREIGN PATENT DOCUMENTS 974,656  2/1951  France.

OTHER PUBLICATIONS

Helmut et al., Chemical Abstracts, vol. 71, 21385k, (1969).

Primary Examiner—Donald G. Daus
Assistant Examiner—Jose Tovar
Attorney, Agent, or Firm—Gerald D. Sharkin; Robert S. Honor; Timothy G. Rothwell

[57] ABSTRACT

The present invention concerns novel 2-(1-piperazinyl)-thiazole derivatives of the formula,

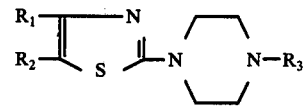

wherein
 $R_1$ is alkyl or cycloalkly,
 $R_2$ is hydrogen or alkyl, and
 $R_3$ is benzyl, alkoxyalkyl or alkoxycarbonyl, or alkyl, alkenyl, alkanoyl or hydroxyalkyl, or acyloxyalkyl, useful as vigilance increasing agents, anorexigenic agents and anti-migraine agents.

41 Claims, No Drawings

ORGANIC COMPOUNDS

This is a continuation of application Ser. No. 437,348 filed Jan. 28, 1974, now abandoned.

The present invention relates to new 2-(1-piperazinyl)-thiazole derivatives.

In accordance with the invention there are provided new compounds of formula I,

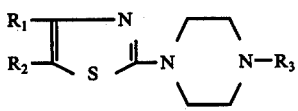

wherein
$R_1$ is alkyl of 2 to 8 carbon atoms or cycloalkyl of 3 to 8 carbon atoms,
$R_2$ is hydrogen or alkyl of 1 to 4 carbon atoms, and
$R_3$ is benzyl, alkoxyalkyl or alkoxycarbonyl having at most 6 carbon atoms in the aggregate thereof, or alkyl, alkenyl, alkanoyl or hydroxyalkyl having at most 4 carbon atoms, or acyloxyalkyl having at most 8 carbon atoms in the aggregate thereof.

$R_1$ preferably signifies straight chain or branched alkyl of 2 to 7 carbon atoms, for example ethyl or a straight chain or branched radical of propyl, butyl, pentyl, hexyl or heptyl, especially, however tert.butyl; $R_1$ is preferably cycloalkyl of 3 to 7 carbon atoms, for example cyclopropyl, cyclobutyl, cyclopentyl, cyclohexyl or cycloheptyl. $R_2$ is preferably hydrogen or straight chain or branched alkyl of 1 to 4 carbon atoms, e.g. methyl, ethyl or a straight chain or branched radical of propyl or butyl. $R_3$ is preferably benzyl, alkoxyalkyl having altogether 3 to 6 carbon atoms, such as methoxyethyl, ethoxyethyl, propoxyethyl, ethoxypropyl, methoxypropyl or propoxypropyl, alkoxycarbonyl having altogether 2 to 6 carbon atoms, e.g. methoxycarbonyl, ethoxycarbonyl, propoxycarbonyl, butoxycarbonyl or pentoxycarbonyl, alkyl of 1 to 4 carbon atoms, e.g. methyl, ethyl or straight chain or branched propyl or butyl, alkenyl of 3 or 4 carbon atoms, such as allyl or methallyl, alkanoyl of 2 to 4 carbon atoms, such as acetyl, propionyl or butanoyl, or hydroxyalkyl of 2 to 4 carbon atoms, such as hydroxyethyl, or straight chain or branched hydroxypropyl or hydroxybutyl. When $R_3$ is acyloxyalkyl the acyl groups preferably contain at most 4 carbon atoms and may be chosen from acetyl, propanoyl and butanoyl.

A carbon containing radical not particularly defined herein otherwise, e.g. alkyl, preferably contains up to 4 carbon atoms.

Further, in accordance with the invention a compound of formula I may be obtained by a process comprising
a. reacting a reactive ester of an alcohol of formula II,

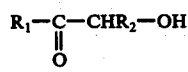

wherein $R_1$ and $R_2$ are as defined above,
with a thiourea of formula III,

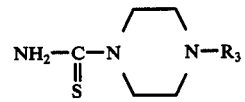

wherein $R_3$ is a defined above, or
b. reacting together a reactive ester of an alcohol of formula II and piperazine or a piperazine derivative of formula IV,

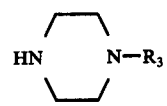

wherein $R_3$ is as defined above,
wherein one of the reaction components is in thiocyanic acid ester form, or
c. introducing the radical $R_3$, which is as defined above, into a compound of formula IX,

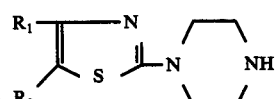

wherein $R_1$ and $R_2$ are as defined above, or
d. acylating a compound of formula Ia,

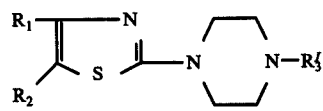

wherein $R_1$ and $R_2$ are as defined above, and $R_3^I$ is hydroxyalkyl,
to produce a compound of formula Ib,

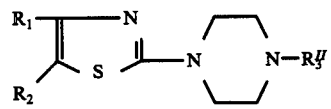

wherein $R_1$ and $R_2$ are as defined above, and $R_3^{II}$ is acyloxyalkyl.

The process of the invention described in section (a) may, for example, be effected as follows The reaction is preferably effected in an inert organic solvent, e.g. an optionally aqueous alcohol such as methanol, ethanol or isopropanol, or in acetone, dioxane, benzene, toluene, xylene or dimethyl formamide. Reactive esters of compounds of formula II which may especially be used are hydrohalic acid esters, especially hydrochloric acid ester or p-toluenesulphonic acid ester. The reaction may be effected by allowing the reaction mixture to stand at room temperature (20° C) or by heating to a temperature up to 120° C, preferably, however, by heating to a temperature between 75° and 100° C. The compound of formula III may be used in acid addition salt form. When a hydrohalic acid ester of a compound of formula II is used, a hydrohalic acid addition salt of the compound of formula I is obtained. When it is desired to obtain a compound of formula I in the form of a base, it is convenient to effect the reaction in the presence of an acid-binding agent, e.g. triethylamine.

The process variant (b) may, for example, be effected as follows

The thiocyanic acid ester may be formed in a preliminary reaction or in situ.

Piperazine or a piperazine derivative of formula IV, or a reactive ester of the alcohol of formula II may be first reacted with thiocyanic acid or a thiocyanate, especially potassium thiocyanate or ammonium thiocyanate, in an inert solvent, e.g. in optionally aqueous ethanol or in dioxane. The reaction may be effected at a temperature between room temperature and 80° C, preferably at 70° C. The subsequent reaction of the thiocyanic acid salt of piperazine or of the piperazine derivative with a reactive ester of the alcohol of formula II or of piperazine or of a piperazine derivative of formula IV, with the thiocyanic acid ester of an alcohol of formula II, is preferably effected in an inert organic solvent, e.g. an optionally aqueous alcohol such as methanol, ethanol or isopropanol, or in acetone, dioxane, benzene, toluene, xylene or dimethyl formamide. The reaction mixture may be maintained at room temperature or heated up to 120° C, preferably, however, heated to a temperature between 75° and 100° C. The intermediate formation of the thiocyanic acid salt of piperazine or of a piperazine derivative or of the thiocyanic acid ester of the alcohol of formula II, having the formula

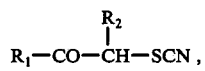

required for the reaction, may also be effected by carrying out the reaction of piperazine or of a piperazine derivative of formula IV with a reactive ester of the alcohol of formula II in the presence of thiocyanic acid or of a thiocyanate under the conditions for the above mentioned subsequent reaction. Reactive esters of compounds of formula II which may especially be used are hydrohalic acid esters, especially hydrochloric acid ester or p-toluenesulphonic acid ester.

The processes of the invention described in section c) may be effected as follows:

The introduction of the radical $R_3$ into a compound of formula IX may, for example, be effected by reacting a compound of formula IX with a reactive derivative, especially a hydrohalic acid ester or a sulphuric acid ester, for example, a dialkyl sulphate of a hydroxy compound of formula $R_3$—OH.

The reaction may be effected in the presence or absence of an inert solvent. A suitable solvent is an alcohol, e.g. ethanol, or benzene, toluene, dioxane or pyridine. The reaction is conveniently effected at a temperature between room temperature and 120° C, preferably between 50° and 80° C. The presence of an acid-binding agent, e.g. 1,8-bis-(dimethylamino)-naphthalene, in this reaction is convenient.

An alkyl group may alternatively be introduced in accordance with the method of reductive alkylation, by reacting a compound of formula IX with a corresponding aldehyde, either by simultaneous reduction with hydrogen in the presence of a catalyst, e.g. platinum oxide conveniently at room temperature, or in the presence of a reducing agent, e.g. formic acid. The latter reaction is preferably effected by dissolving the unsubstituted compound in 90% formic acid and heating with the corresponding aldehyde to a temperature between 50° and 150° C, preferably to the boil.

For the introduction of an e.g. β or α hydroxyalkyl group, the compound of formula IX may alternatively be reacted with a β or α or alkylene oxide. The reaction is preferably effected in an organic solvent, e.g. an alcohol such as methanol. Suitably the reaction is effected at a temperature of 0° to room temperature (25° C).

An acyl group may be introduced by reacting with an acyl halide or acylanhydride. The reaction may be carried out in benzene. The reaction temperature is conveniently the reflux temperature of the reaction mixture, e.g. between 60° and 150°.

Process variant d) may be effected according to conventional acylation processes, e.g. with an acid anhydride or an acid halide, for example an acid chloride or acid bromide. The reaction may be effected in a solvent such as benzene or pyridine. The reaction temperature is conveniently from 20° to 100° C preferably 50° to 60°.

The hydrohalic acid esters of the alcohols of formula II, used as starting materials in the process variants (a) and (b), are known or may be produced in known manner. These compounds may be obtained by reacting a carboxylic acid chloride of formula VII,

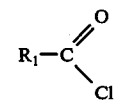

wherein $R_1$ is as defined above,
with a corresponding diazoalkane, and treating the resulting diazoketone with a hydrohalic acid. Hydrohalic acid esters of an alcohol of formula II, having a tert.carbon atom adjacent to the carbonyl group ($R_1$ = tert.alkyl), may also be obtained by direct halogenation, e.g. with halogen or a halogenating agent such as sulphuryl chloride, of the corresponding alkylketone. It is not essential to isolate the ester before subsequent reaction with the thiourea derivative of formula III.

Other esters of an alcohol of formula II, e.g. toluenesulphonic acid esters, may, for example, be obtained by reacting the corresponding hydrohalic acid ester with a salt, especially the sodium salt, of a corresponding acid, e.g. of toluenesulphonic acid.

The thiourea derivatives of formula III further used as starting materials in process variant a) are known or may be produced in known manner, e.g. by reacting a piperazine derivative of formula IV conveniently at an elevated temperature with a conveniently concentrated aqueous solution of ammonium thiocyanate. The piperazine derivatives of formula IV, used as starting materials in process variant (b), are also known or may be produced in known manner.

Some of the compounds of formula IX, used as starting materials in the process variant (c), are known and have been described in Swiss Pat. Spec. No. 462,176. Insofar as these compounds are unknown, they may be produced in a manner analogous to the compounds of formula I, for example by using a thiourea derivative of piperazine in process variant (a), in place of a compound of formula III, or piperazine in process variant (b), in place of compounds of formula IV.

Insofar as the production of the starting materials is not particularly described, these compounds are known or may be produced and purified in accordance with known processes, or in a manner analogous to the processes described herein or to known processes.

The compounds of formula I, obtained in accordance with the invention, may be isolated in known manner, e.g. by extraction, precipitation or salt formation, and may then be purified in known manner, e.g. by recrystallization.

In the following non-limitative Examples all temperatures are indicated in degrees Centigrade, room temperature is between 20° and 30° C, unless otherwise indicated. The vacuum used is between 8 and 20 mm Hg, unless otherwise indicated.

EXAMPLE 1:
2-(4-methyl-1-piperazinyl)-4-tert.butyl-thiazole [process variant a)]

1.34 g of chloropinacoline are dissolved in 15 cc of absolute ethanol. After the addition of 1.6 g of 4-methyl-1-piperazinyl-thiocarboxamide, the mixture is heated to the boil on a water bath for 1 hour. Cooling is then effected and diethyl ether is added until the mixture remains turbid. The precipitated crystals are filtered off and recrystallized from ethanol. The resulting 2-(4-methyl-1-piperazinyl)-4-tert.butyl-thiazole hydrochloride has an M.P. of 206°. The base liberated from its hydrochloride in known manner by treatment with an aqueous sodium hydroxide solution has a B.P. of 97°-99°/0.2 mm Hg.

EXAMPLE 2:
2-(4-methyl-1-piperazinyl)-4-cyclohexyl-thiazole 4.8 g of chloromethyl-cyclohexyl-ketone are dissolved in 25 cc of absolute ethanol, and 4.8 g of 4-methyl-1-piperazinyl-thiocarboxamide are added to the resulting solution. The mixture is then heated to the boil at reflux for 3 hours, hydrochloric acid in ethanol is subsequently added until a weakly acid reaction is obtained, filtration and cooling with ice are effected. The precipitated crystals are recrystallized from absolute ethanol with the addition of isopropyl ether while treating with active charcoal. The resulting 2-(4-methyl-1-piperazinyl)-4-cyclohexyl-thiazole hydrochloride has an M.P. between 205° and 210°. The corresponding free base is obtained in known manner from the hydrochloride by treatment with an aqueous sodium hydroxide solution.

EXAMPLE 3:
2-[4(2-hydroxyethyl)-1-piperazinyl]-4-tert.butyl-thiazole 5 g of 4-(2-hydroxyethyl)-1-piperazinyl-thiocarboxamide are added to a solution of 3.6 g of bromopinacoline in 70 cc of ethanol, and the reaction mixture is subsequently heated to the boil at reflux for 2 hours. The mixture is then concentrated by evaporation in a vacuum. The residue is dissolved in a small amount of water and is divided between chloroform and a concentrated aqueous sodium hydroxide solution. The chloroform phase is washed with water, dried over sodium sulphate and concentrated by evaporation in a vacuum. Hydrochloric acid in ethanol is added to the resulting oil and the solution is concentrated by evaporation. After recrystallizing the residue from a small amount of ethanol/diethyl ether, 2-[4-(2-hydroxyethyl)-1-piperazinyl]-4-tert.butyl-thiazole dihydrochloride, having a M.P. of 133°-142°, is obtained. The free base is obtained is known manner from the dihydrochloride by treatment with an aqueous sodium hydroxide solution.

EXAMPLE 4:
2-(4-methyl-1-piperazinyl)-4-isopropyl-thiazole 3.6 g of 1-chloro-3-methyl-butan-2-one are dissolved in 25 cc of absolute ethanol, and 4.8 g of 4-methyl-1-piperazinyl-thiocarboxamide are added to the resulting solution. The resulting reaction mixture is subsequently heated to the boil at reflux for 2 hours, is then filtered whilst hot, hydrochloric acid in ethanol is added until an acid reaction is obtained, and cooling is effected in an ice bath. The resulting crystals are filtered off and recrystallized from absolute ethanol. The resulting 2-(4-methyl-1-piperazinyl)-4-isopropyl-thiazole dihydrochloride begins to melt at 140°. The free base is obtained in known manner from the dihydrochloride by treatment with an aqueous sodium hydroxide solution.

EXAMPLE 5:
2-(4-methyl-1-piperazinyl)-4-tert.butyl-thiazole [process variant b)]

7.6 g of ammonium thiocyanate are added to a solution of 10.5 g of N-methylpiperazine in 50 cc of ethanol. After heating on a water bath for 15 minutes, the reaction mixture is concentrated in a vacuum and the resulting crystals are separated.

15.5 of the resulting N-methylpiperazine thiocyanate and 13.4 of chloropinacoline are heated on a water bath for 8 hours in 50 cc of ethanol. After concentrating the reaction mixture and adding ethyl acetate, the separated crystals are filtered off and recrystallized from ethanol. The resulting 2-(4-methyl-1-piperazinyl)-4-tert.butyl-thiazole hydrochloride has an M.P. between 205° and 206°. The free base is obtained in known manner from the hydrochloride by treatment with an aqueous sodium hydroxide solution.

EXAMPLE 6:
2-(4-ethoxycarbonyl-1-piperazinyl)-4-tert.butyl-thiazole 5.4 g of potassium thiocyanate are added to a solution of 9 g of bromopinacoline in 50 cc of ethanol. The resulting mixture is heated on a water bath for 10 minutes, 7.9 g of N-ethoxycarbonylpiperazine are subsequently added, and the mixture is heated for a further 4 hours. After separating the resulting potassium bromide, the reaction mixture is concentrated, the residue is taken up in ether, and hydrochloric acid in ethanol is added until a weakly acid reaction is obtained. 2-(4-ethoxycarbonyl-1-piperazinyl)-4-tert.butyl-thiazole hydrochloride, having an M.P. of 145°-150° after recrystallization from ethyl acetate, is obtained. The base is obtained in known manner from the hydrochloride by treatment with an aqueous sodium hydroxide solution.

EXAMPLE 7:
2-(4-acetyl-1-piperazinyl)-4-tert.butyl-thiazole [process variant c)]

a. 2-piperazinyl-4-butyl-thiazole

By using the process described in Example 1, but replacing 4-methyl-1-piperazinyl-thiocarboxamide by an equivalent amount of 1-piperazinyl-thiocarboxamide, 2-piperazinyl-4-tert.buty-thiazole dihydrochloride, having a M.P. of 190°-196°, is obtained. The free base is obtained therefrom by treatment with an aqueous sodium hydroxide solution.

b. 2-(4-acetyl-1-piperazinyl)-4-tert.butyl-thiazole 1.1 g of 2-piperazinyl-4-tert.butyl-thiazole are dissolved in 15 cc of absolute benzene, 10 cc of acetic anhydride are added to the resulting solution, and the mixture is heated to the boil at reflux for 1 hour. The residue obtained after concentrating the reaction mixture by evaporation is divided between diethyl ether/isopropanol (2:1) and an 8 N aqueous sodium hydroxide solution. The organic phase is separated, and hydrochloric acid in ethanol is added to the filtrate until an acid reaction is obtained. The precipitated crystals are recrystallized from isopropyl ether/ethanol, whereby 2-(4-acetyl-1-piperazinyl)-4-tert.butyl-thiazole hydrochloride, having an M.P. of 140°–152°, is obtained. The free base is obtained in known manner from the hydrochloride by treatment with an aqueous sodium hydroxide solution.

EXAMPLE 8:
2-(4-methyl-1-piperazinyl)-4-tert.butyl-thiazole 1.26 g of dimethyl sulphate are added to 2.25 g of 2-piperazinyl-4-tert.butyl-thiazole in 15 cc of absolute benzene in the absence of moisture. The reaction mixture is kept at 80° for 15 hours, is then cooled and divided between diethyl ether and an 8 N aqueous sodium hydroxide solution. The ethereal solution is then dried over sodium sulphate, filtered, and hydrochloric acid in ethanol is added to the filtrate until a weakly acid reaction is obtained. The mixture is then evaporated to dryness. The residue is recrystallized twice from absolute ethanol, whereby 2-(4-methyl-1-piperazinyl)-4-tert.butyl-thiazole hydrochloride, having an M.P. of 200°–204°, is obtained. The free base is obtained in known manner from the hydrochloride by treatment with an aqueous sodium hydroxide solution.

EXAMPLE 9:
2-[4-(2-hydroxyethyl)-1-piperazinyl]-4-tert.butyl-thiazole

A solution of 2.25 of 2-piperazinyl-4-tert.butyl-thiazole in 20 cc of 95% methanol is cooled to 0°, and 0.6 g of ethylene oxide are added. After heating slowly to room temperature, the reaction mixture is allowed to stand at this temperature for 2 hours and is then evaporated to dryness. The resulting oily residue is dissolved in a small amount of absolute ethanol, hydrochloric acid in ethanol is added until an acid reaction is obtained, the solvent is removed and crystallization is effected from absolute ethanol/diethyl ether. 2-[4-(2-hydroxyethyl)-1-piperazinyl]-4-tert.butyl-thiazole dihydrochloride, having an M.P. of 142°, is obtained. The free base is obtained in known manner from the dihydrochloride by treatment with an aqueous sodium hydroxide solution.

EXAMPLE 10:
2-(4-benzyl-1-piperazinyl)-4-tert.butyl-thiazole [process variant a)]

4.7 g of 4-benzyl-1-piperazinylthiocarboxamide and 3.6 g of bromopinacoline are heated to the boil at reflux for 2 hours in 20 cc of absolute ethanol. The reaction mixture is subsequently cooled, whereby crystalline 2-(4-benzyl-1-piperazinyl)-4-tert.butyl-thiazole hydrochloride, having an M.P. between 266° and 268° (with decomp.), is obtained. The free base is obtained in known manner from the hydrobromide by treatment with an aqueous sodium hydroxide solution.

EXAMPLE 11:
2-[4-(2-methoxyethyl-1-piperazinyl]-4-tert.butyl-thiazole 4.3 g of 4-(2-methoxyethyl)-1-piperazinylthiocarboxamide and 3.1 g of bromopinacoline are heated to the boil at reflux for 3 hours in 25 cc of ethanol. The resulting clear solution is subsequently concentrated by evaporation in a vacuum, and an 8 N aqueous sodium hydroxide solution is added to the residue. Extraction is subsequently effected with diethyl ether and hydrochloric acid in ethanol is added to the ethereal solution until an acid reaction is obtained. 2-[4-(2-methoxyethyl)-1-piperazinyl]-4-tert.butyl-thiazole dihydrochloride crystallizes and has an M.P. of 181°–191° after recrystallization from ethanol/ethyl acetate. The free base is obtained in known manner from the dihydrochloride by treatment with an aqueous sodium hydroxide solution.

EXAMPLE 12:
2-[4-(2-hydroxyethyl)-1-piperazinyl]-4-cyclopentyl-thiazole 5 g of 4-(2-hydroxyethyl)-1-piperazinylthiocarboxamide and 4 g of chloromethyl-cyclopentylketone are heated to the boil for 3 hours in 25 cc of ethanol. A small amount of hydrochloric acid in ethanol and isopropyl ether are subsequently added to the mixture and this is cooled, whereby 2-[4-(2-hydroxyethyl)-1-piperazinyl]-4-cyclopentyl-thiazole dihydrochloride crystallizes and has an M.P. of 175°–177° after recrystallization from ethanol. The free base is obtained in known manner from the dihydrochloride by treatment with an aqueous sodium hydroxide solution.

The compounds of formula I wherein $R_1$ is as defined below, $R_2$ is hydrogen and $R_3$ is methyl, are obtained by using the processes described in Examples 1 to 12:

| Example | $R_1$ | M.P. of the dihydrochloride form of the compound of formula I |
|---|---|---|
| 13 | ethyl | 215–218° |
| 14 | sec.butyl | 162–166° |
| 15 | isobutyl | 162–166° |
| 16 | n-butyl | 170–174° |
| 17 | cyclopropyl | 160–168° |
| 18 | cyclobutyl | 244–246° |
| 19 | cyclopentyl | 160° (beginning of melting) |
| 20 | cycloheptyl | 209–212° |
| 21 | n-heptyl | 164–166° |

The free bases are obtained in known manner from the dihydrochlorides by treatment with an aqueous sodium hydroxide solution.

EXAMPLE 22:
2-[4-(2-acetoxyethyl)-1-piperazinyl]-4-tert.butyl-thiazole [process variant d)]

3 g of 2-[4-(2-hydroxyethyl)-1-piperazinyl]-4-tert.butyl-thiazole and 1.2 g of acetic anhydride are heated to 50°–60° for 10 hours in 10 cc of benzene. The reaction mixture is subsequently concentrated by evaporation in a vacuum and the resulting oil is taken up in ether. Hydrochloric acid in ether is added, whereby 2-[4-(2-acetoxyethyl)-1-piperazinyl]-4-tert.butyl-thiazole is obtained as monohydrochloride in crystalline form. After recrystallization from ethyl acetate, the salt form has an M.P. of 184°–185°.

EXAMPLE 23:
2-(4-allyl-1-piperazinyl)-4-tert.butyl-thiazole [process variant a)]

3.7 g of 4-allyl-1-piperazinyl-thiocarboxamide are added to a solution of 3.6 g of bromopinacoline in 40 cc of ethanol, and the reaction mixture is subsequently heated to the boil at reflux for 2 hours. The mixture is subsequently concentrated by evaporation in a vacuum, the residue is dissolved in a small amount of water and divided between ether and a concentrated aqueous sodium hydroxide solution. The ether phase is washed with water, dried over sodium sulphate and saturated with hydrogen chloride gas after filtration. The monohydrochloride of 2-(4-allyl-1-piperazinyl)-4-tert.butyl-thiazole crystallizes and has an M.P. of 212°–214° after recrystallization from ethanol/diisopropyl ether.

EXAMPLE 24:
2-(4-methyl-1-piperazinyl)-4-tert.butyl-5-methyl-thiazole 3.9 g of 2-bromo-4-dimethyl-pentan-3-one are dissolved in 10 cc of absolute ethanol and heated to the boil for 5 hours after the addition of 3.2 g of 4-methyl-1-piperazinyl-thiocarboxamide. The monohydrobromide form of 2-(4-methyl-1-piperazinyl)-4-tert.butyl-5-methyl-thiazole crystallizes upon cooling and has an M.P. of 205° after recrystallization from absolute ethanol. The dihydrochloride has an M.P. of 200°–202° after recrystallization from ethanol.

The compounds of formula I have not been described in the literature.

The compounds of formula I are useful because they possess pharmacological activity in animals. In particular, the compounds of formula I are useful as vigilance-increasing agents and stimulating agents, as indicated by standard tests, for example, by an increased spontaneous activity in mice and rats on p.o. administration of from 0.2 to 5 mg/kg animal body weight of the compounds in accordance with the method described by Caviezel and Baillod in Pharm. Acta. Helv. 33, 465 (1958).

The compounds of formula I are furthermore useful as appetite-suppressant and anorexigenic agents, e.g. for the treatment of obesity, as in standard tests, for example by a reduction of feed activity in mice and rats on p.o. administration of from 0.2 to 5 mg/kg animal body weight of the compounds in accordance with the method described by Stille and Lauener in Helv. Physiol. Acta. 22, c 46–47 (1964).

The compounds of formula I are furthermore useful as serotonin antagonistic agents, e.g. for the treatment of migraine, as indicated in standard tests, for example, in the isolated rat uterus test on administration of from 0.001 and 0.1 μg/ml of the compounds and in the rat paw odema test on i.p. administration of from 1 to 30 mg/kg animal body weight of the compounds.

For all the above mentioned uses the dosage will, of course, vary depending on the compound employed, mode of administration and treatment desired. However, in general, satisfactory results are obtained when administered at a daily dosage of from about 0.1 mg to about 30 mg per kg animal body weight, conveniently given in divided doses 2 to 4 times a day or in sustained release form. For the larger mammals, the total daily dosage is in the range from about 5 to about 2000 mg, and dosage forms suitable for oral administration comprise from about 1 mg to about 1000 mg of the compounds admixed with a solid or liquid pharmaceutical carrier or diluent.

The compound of Example 1 has especially interesting properties for the above-mentioned uses.

The compounds of formula I may be administered in pharmaceutically acceptable acid addition salt form. Such acid addition salt forms exhibit the same order of activity as the free base forms and are readily prepared in conventional manner. Representative acids for salt formation include organic acids such as maleic, fumaric and tartaric acids and methane sulphonate and mineral acids such as hydrochloric, hydrobromic and sulphuric acids. A pharmaceutical composition may comprise a compound of formula I, in free base form or in pharmaceutically acceptable acid addition salt form, in association with a pharmaceutical carrier or diluent. Such compositions conveniently contain more than 1% by weight of the compound of formula I and may be prepared by conventional techniques to be in conventional forms, for example, capsules, tablets, suppositories, dispersible powders, syrups, elixirs, suspensions or solutions, for enteral or parenteral administration. Suitable pharmaceutical diluents or carriers include, for example, water, alcohols, natural or hardened oils and waxes, calcium and sodium carbonates, calcium phosphate, kaolin, talc and lactose as well as suitable preserving agents, such as ethyl-p-hydroxybenzoate, suspending agents such as methyl cellulose, tragacanth and sodium alginate, wetting agents such as lecithin, polyoxyethylene stearate and polyoxyethylene sorbitan mono-oleate, granulating and disintegrating agents such as starch and alginic acid, binding agents such as starch, gelatin and acacia, and lubricating agents such as magnesium stearate, stearic acid and talc, in order to provide an elegant and palatable pharmaceutical preparation. Compositions in tablet form may be coated by conventional techniques to delay disintegration of the tablet and absorption of the active ingredient in the gastrointestinal tract and thereby provide sustained action over a long period.

The preferred compositions from the standpoint of ease of administration are solid compositions, particularly solid-filled gelatin capsules and tablets.

I claim:
1. A compound of the formula

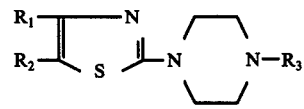

where
$R_1$ is t-butyl or cycloalkyl of 3 to 8 carbon atoms,
$R_2$ is hydrogen or alkyl of 1 to 4 carbon atoms,
and
$R_3$ is benzyl, alkoxyalkyl or alkoxycarbonyl having at most 6 carbon atoms in the aggregate thereof, or alkyl, alkenyl, alkanoyl or hydroxyalkyl having at most 4 carbon atoms, or alkanoyloxy alkyl having at most 8 carbon atoms in the aggregate thereof
or a pharmaceutically acceptable acid addition salt thereof.

2. The compound which is 2-(4-methyl-1-piperazinyl)-4-tert.butyl-thiazole.

3. The compound of claim 1 which is 2-(4-methyl-1-piperazinyl)-4-cyclohexyl-thiazole.

4. The compound of claim 1 which is 2-[4-(2-hydroxyethyl)-1-piperazinyl]-4-tert.butylthiazole.

5. The compound of claim 1, which is 2-(4-ethoxycarbonyl-1-piperazinyl)-4-tert.butyl-thiazole.

6. The compound of claim 1, which is 2-(4-acetyl-1-piperazinyl)-4-tert.butyl-thiazole.

7. The compound of claim 1, which is 2-(4-benzyl-1-piperazinyl)-4-tert.butyl-thiazole.

8. The compound of claim 1, which is 2-[4-(2-methoxyethyl)-1-piperazinyl]-4-tert.butylthiazole.

9. The compound of claim 1, which is 2-[4-(2-hydroxyethyl)-1-piperazinyl]-4-cyclopentylthiazole.

10. The compound which is 2-(4-methyl-1-piperazinyl)-4-sec.butyl-thiazole.

11. The compound which is 2-(4-methyl-1-piperazinyl)-4-isobutyl-thiazole.

12. The compound which is 2-(4-methyl-1-piperazinyl)-4-n-butyl-thiazole.

13. The compound of claim 1 which is 2-(4-methyl-1-piperazinyl)-4-cyclopropyl-thiazole.

14. The compound of claim 1 which is 2-(4-methyl-1-piperazinyl)-4-cyclobutyl-thiazole.

15. The compound which is 2-(4-methyl-1-piperazinyl)-4-cyclopentyl-thiazole.

16. The compound of claim 1 which is 2-(4-methyl-1-piperazinyl)-4-cycloheptyl-thiazole.

17. The compound of claim 1 which is 2-(4-methyl-1-piperazinyl)-4-n-heptyl-thiazole.

18. The compound of claim 1 which is 2-[4-(2-acetoxyethyl)-1-piperazinyl]-4-tert.butylthiazole.

19. The compound of claim 1 which is 2-(4-allyl-1-piperazinyl)-4-tert.butyl-thiazole.

20. The compound of claim 1, which is 2-(4-methyl-1-piperazinyl)-4-tert.butyl-5-methylthiazole.

21. A compound of claim 1, wherein $R_2$ is hydrogen.

22. A compound of claim 1, wherein $R_3$ is benzyl.

23. A compound of claim 1, wherein $R_3$ is alkoxyalkyl.

24. A compound of claim 1, wherein $R_3$ is alkoxycarbonyl.

25. A compound of claim 1, wherein $R_3$ is alkyl.

26. A compound of claim 1, wherein $R_3$ is alkenyl.

27. A compound of claim 1, wherein $R_3$ is alkanoyl.

28. A compound of claim 1, wherein $R_3$ is hydroxyalkyl.

29. A compound of claim 1, wherein $R_3$ is alkanoyloxyalkyl.

30. A pharmaceutical composition consisting essentially of a compound of claim 1 in association with a pharmaceutical carrier or diluent.

31. A method of increasing vigilance in animals which comprises administering a therapeutically effective amount of a compound of claim 1 to an animal in need of such treatment.

32. A method of treating obesity in animals which comprises administering a therapeutically effective amount of a compound of claim 1 to an animal in need of such treatment.

33. A method of treating migraine in animals which comprises administering a therapeutically effective amount of a compound of claim 1 to an animal in need of such treatment.

34. A method of increasing vigilance in animals which comprises administering a therapeutically effective amount of the compound of claim 2 to an animal in need of such treatment.

35. A method according to claim 34 in which 5 to 2000 milligrams of the compound are administered daily.

36. A method according to claim 34 in which 1 to 1000 milligrams of the compound are administered per unit dose.

37. A pharmaceutical composition useful in increasing viligance consisting essentially of the compound of claim 2 with a pharmaceutical carrier or diluent.

38. A pharmaceutical composition according to claim 37 comprising 1 to 1000 milligrams per unit dosage.

39. A compound of claim 1 wherein $R_1$ is t-butyl.

40. A compound of claim 1 wherein $R_1$ is cyclopentyl.

41. A compound of claim 1 wherein $R_1$ is cycloalkyl.

* * * * *